United States Patent [19]

Mendoza

[11] 4,310,688
[45] Jan. 12, 1982

[54] REDUCTION OF HYDROLYZABLE CHLORIDE IMPURITIES IN AN ISOCYANATOALKYL ESTER OF AN ORGANIC CARBOXYLIC ACID

[75] Inventor: Abel Mendoza, Midland, Mich.

[73] Assignee: The Dow Chemical Company, Midland, Mich.

[21] Appl. No.: 87,594

[22] Filed: Oct. 22, 1979

[51] Int. Cl.³ .............................................. C07C 67/14
[52] U.S. Cl. .................................. 560/222; 260/404; 560/105; 560/106; 560/107; 560/110; 560/218; 560/220; 560/221; 560/254; 560/255; 560/262; 560/266
[58] Field of Search ............... 560/222, 218, 105, 106, 560/107, 110, 266, 221, 254, 255, 262, 220; 260/453 SP, 404

[56] References Cited

U.S. PATENT DOCUMENTS

| | | | |
|---|---|---|---|
| 2,718,516 | 9/1955 | Bortnick | 526/312 |
| 2,821,544 | 1/1958 | Holtschmidt | 560/213 |
| 3,465,023 | 9/1969 | Kamal | 260/453 PH |
| 3,793,362 | 2/1974 | Kolakowski et al. | 260/453 SP |
| 4,094,894 | 6/1978 | Blackwell | 260/453 SP |
| 4,118,286 | 10/1978 | Burns et al. | 260/453 SP |
| 4,146,550 | 3/1979 | Reichmann | 260/453 P |

FOREIGN PATENT DOCUMENTS

| | | |
|---|---|---|
| 771179 | 11/1967 | Canada .................................. 560/222 |
| 1252099 | 11/1971 | United Kingdom . |
| 1280007 | 7/1972 | United Kingdom . |
| 1458747 | 12/1976 | United Kingdom . |

*Primary Examiner*—Natalie Trousof
*Assistant Examiner*—L. Hendriksen
*Attorney, Agent, or Firm*—Michael L. Glenn

[57] ABSTRACT

The level of hydrolyzable chloride-containing impurities in an isocyanatoalkyl ester of an organic carboxylic acid is reduced by reacting the impurities with a vicinal epoxide-containing compound and then fractionally distilling the mixture to recover the isocyanatoalkyl ester. As an example, crude 2-isocyanatoethyl methacrylate (IEM) in a methylene chloride solution containing 0.084 weight percent of hydrolyzable chloride is contacted with a diglycidyl ether of bisphenol A at 23° C. This reaction mixture is then fractionally distilled to separate the IEM from the methylene chloride first cut and the epoxy resin residue. The hydrolyzable chloride level of the distilled IEM product is only 0.03 weight percent.

15 Claims, No Drawings

REDUCTION OF HYDROLYZABLE CHLORIDE IMPURITIES IN AN ISOCYANATOALKYL ESTER OF AN ORGANIC CARBOXYLIC ACID

BACKGROUND OF THE INVENTION

1. Field of the Invention

This is a novel process for reducing the hydrolyzable chloride content of an isocyanatoalkyl ester of an organic carboxylic acid. In particular this process relates to the use of alkylene oxide or an epoxy resin as hydrogen chloride scavengers in such a process.

2. Prior Art

Isocyanatoalkyl esters of organic carboxylic acids can be prepared by reacting phosgene with various specific amines or nitrogen-containing compounds. British Pat. Nos. 1,280,007 and 1,252,099 and U.S. Pat. No. 2,821,544 describe different methods of preparation of these isocyanatoalkyl esters involving the phosgenation of nitrogen-containing compounds and are incorporated herein by reference. U.S. Pat. No. 2,718,516 discloses the preparation of 2-isocyanatoethyl methacrylate by a different reaction sequence and is also incorporated herein by reference.

The above-described methods of preparation all produce adducts of the isocyanatoalkyl esters and hydrogen chloride (believed to be carbamoyl chlorides) as co-products in addition to the esters themselves. These hydrogen chloride adducts contain hydrolyzable chloride, which is known to have an adverse impact on the reaction of the isocyanatoalkyl esters with hydroxyl, mercapto, amino and other active hydrogen functionalities.

Various techniques have been proposed in the literature to remove hydrolyzable chloride from specific isocyanates. U.S. Pat. No. 3,465,023 teaches that the use of an aqueous solution of a weak base reduces the hydrolyzable chloride content of an aliphatic isocyanate. Heating an organic isocyanate in the presence of an organic sulfonic acid or ester is disclosed in British Pat. No. 1,458,747 to remove hydrolyzable chloride-containing impurities. U.S. Pat. No. 3,793,362 describes a process for reducing the acidity and hydrolyzable chloride levels in polymethylene polyphenylisoycanates by treatment with a monomeric epoxide. However, only minor reductions in the hydrolyzable chloride level is attained by this epoxide treatment and no separation of the isocyanate compound from the residue of the epoxide compound is effected. Other methods for reducing the hydrolyzable chloride content of specific isocyanates are taught in U.S. Pat. Nos. 4,094,894; 4,118,286 and 4,146,550.

None of the aforementioned techniques for removing hydrolyzable chlorides are explicitly stated to be applicable to isocyanatoalkyl esters of organic carboxylic acids. Furthermore, some of these techniques are not operable with polymerizable isocyanates, such as 2-isocyanatoethyl methacrylate, because the high temperatures and pressures employed will effect substantial polymerization. The only method employed in the prior art to purify these isocyanatoalkyl esters is fractional distillation. Such fractional distillations are only moderately effective. In many utilities, the isocyanatoalkyl ester must contain less than 500 parts per million by weight of hydrolyzable chloride. Removal of this low residual levels of hydrolyzable chloride generally cannot be effected in a single fractional distillation.

SUMMARY OF THE INVENTION

According to this invention, the hydrolyzable chloride content of an isocyanatoalkyl ester of an organic acid is reduced in a process comprising:

(a) contacting the isocyanatoalkyl ester in the liquid phase with a vicinal epoxide-containing compound, said epoxide-containing compound being present in a ratio of at least about 0.5 equivalent of epoxide per equivalent of hydrolyzable chloride, so as to effect substantial reaction of the epoxide-containing compound with the hydrolyzable chloride; and (b) separating the isocyanatoalkyl ester from the other components of the reaction mixture in step (a) by fractional distillation.

DETAILED DESCRIPTION OF THE INVENTION

Isocyanatoalkyl Ester Reactants:

The isocyanatoalkyl esters of this invention form a known class of compounds having many members, which can be represented by the formula

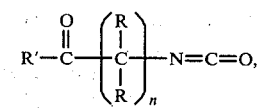

wherein each R is independently hydrogen, alkyl, alkenyl, alkoxy, alkaryl, aralkyl or aryl; R' is hydrogen, a $C_1$–$C_{17}$ alkyl, a $C_2$–$C_{17}$ alkenyl, a $C_7$–$C_{20}$ aralkyl or a $C_6$–$C_{24}$ aryl; and n is 2 or 3. Of course, R in the above formula can represent a wide variety of moieties, such as, methyl, ethyl, cyclohexyl, isopropenyl, vinyl, ethoxy, tolyl, xylyl, phenylethyl or phenyl. Preferably, R is hydrogen and n is 2. R' also has myriad possible identities, for example, ethyl, methyl, propyl, vinyl, isopropenyl, tolyl or phenyl. Preferably, R' is a $C_1$–$C_4$ alkyl or a $C_1$–$C_4$ alkenyl. More preferably, R' is vinyl or isopropenyl, most preferably isopropenyl.

The isocyanatoalkyl ester can conveniently be prepared by any one of the prior art techniques previously mentioned or by other methods known to the art which co-produce hydrolyzable chloride impurities. The instant process is particularly effective with isocyanatoalkyl esters containing at least 0.05 weight percent of hydrolyzable chloride based on the weight of the isocyanatoalkyl ester. In a preferred embodiment, the isocyanatoalkyl ester is prepared by reacting a 2-oxazoline or 2-oxazine in a water-immiscible solvent with phosgene in the presence of an aqueous solution of a hydrogen chloride acceptor, as is described in British Pat. No. 1,252,099. On completion of the phosgenation reaction, the organic phase is conveniently separated, optionally dried with a conventional drying agent, such as $CaCl_2$ or zeolite, and then the epoxide-containing compound is introduced to the organic phase, as set out hereinafter. In one especially preferred embodiment, a 2-oxazoline in an aqueous solution is added with mixing to a water-immiscible organic solvent containing phosgene in the above-described manner.

The hydrolyzable chloride content present as an impurity in the isocyanatoalkyl ester is determined by hydrolyzing the carbamoyl chloride in an aqueous-methanol-toluene medium, followed by titration of the chloride ion present with silver nitrate. This determination is well-known in the art and is set out in American Society for Testing and Materials (ASTM) Test D-1638-78, as it is employed for toluene diisocyanate. This standard test is readily adapted to the determination of hydrolyzable chloride impurities present in an isocyanatoalkyl ester, as is elucidated in the experimental section hereafter.

Vicinal Epoxide Reactant:

The vicinal epoxide-containing compounds used as reactants are likewise well-known compounds. The vicinal epoxide reactants are organic compounds bearing one or more moieties corresponding to the formula

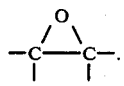

They can be mono- or polyepoxides and can optionally be substituted provided the substituent is not a group reactive with isocyanates. The alkylene oxides of from 2 to about 24 carbon atoms and the epoxy resins are the best known members of this class. Desirably, the boiling point of the epoxide is sufficiently different from that of the isocyanate ester so that these components can be readily separated by distillation.

The preferred monoepoxides are ethylene oxide, 1,2-propylene oxide and 1,2-butylene oxide. These preferred monoepoxides and their reaction products with hydrogen chloride are significantly more volatile than the isocyanate ester and therefore, can be readily separated from the isocyanate ester by fractional distillation.

The most useful epoxy reactants are the polyepoxides, particularly epoxy resins. These polyepoxide reactants are organic compounds possessing more than one vicinal epoxide group per molecule. These polyepoxides can be saturated or unsaturated aliphatic or cycloaliphatic, aromatic or heterocyclic in nature. The polyepoxides are conveniently described in terms of epoxy equivalent values, as defined in U.S. Pat. No. 2,633,458. Various examples of polyepoxides that may be used in the invention are also given in U.S. Pat. No. 2,633,458 and it is to be understood that so much of the disclosure of that patent relative to examples of polyepoxides is incorporated by reference into this specification.

Representative examples of polyepoxides include the glycidyl ethers of novolac resins, i.e., phenol-aldehyde condensates. Preferred resins of this type are those of the formula tion of these polyepoxides is illustrated in U.S. Pat. Nos. 2,616,099 and 2,658,885.

Other examples of polyepoxides include the epoxidized esters of the polyethylenically unsaturated monocarboxylic acids, such as epoxidized linseed, soybean, perilla, oiticica, tung, walnut and dehydrated castor oil, methyl linoleate, butyl linoleate, ethyl 9,12-octadecanedioate, butyl 9,12,15-octadecanetrioate, butyl oleostearate, mono- or diglycerides of tung oil, monoglycerides of soybean oil, sunflower oil, rapeseed oil, hempseed oil, sardine oil, cottonseed oil, and the like.

Another group of the epoxy-containing materials used in the process of the invention include the epoxidized esters of unsaturated monohydric alcohols and polycarboxylic acids, such as, for example, diglycidyl phthalate, diglycidyl adipate, diglycidyl isophthalate, di(2,3-epoxybutyl)adipate, di(2,3-epoxybutyl)oxalate, di(2,3-epoxyhexyl)succinate, di(3,4-epoxybutyl)maleate, di(2,3-epoxyoctyl)pimelate, di(2,3-epoxybutyl)phthalate, di(2,3-epoxyoctyl)tetrahydrophthalate, di(4,5-epoxydodecyl)maleate, di(2,3-epoxybutyl)terephthalate, di(2,3-epoxypentyl)thiodipropionate, di(5,6-epoxytetradecyl)diphenyldicarboxylate, di(3,4-epoxyheptyl)sulfonyldibutyrate, tri(2,3-epoxybutyl)1,2,4-butanetricarboxylate, di(5,6-epoxypentadecyl)tartrate, di(4,5-epoxytetradecyl)maleate, di(2,3-epoxybutyl)azelate, di(3,4-epoxybutyl)citrate, di(5,6-epoxyoctyl)cyclohexane-1,3-dicarboxylate, di(4,5-epoxyoctadecyl)malonate.

Another group of the epoxy-containing materials include those epoxidized esters of unsaturated alcohols and unsaturated carboxylic acids, such as glycidyl glycidate; 2,3-epoxybutyl 3,4-epoxypentanoate; 3,4-epoxyhexyl 3,4-epoxypentanoate; 3,4-epoxy-6-methylcyclohexylmethyl 3,4-epoxy-6-methylcyclohexane carboxylate.

Still another group of the epoxy-containing materials includes epoxidized derivatives of polyethylenically unsaturated polycarboxylic acids, such as, for example, dimethyl 8,9,12,13-diepoxyeicosanedioate; dibutyl 7,8,11,12-diepoxyoctadecanedioate; dioctyl 10,11-diethyl-8,9,12,13-diepoxyeicosanedioate; dihexyl 6,7,10,11-diepoxyhexadecanedioate; didecyl 9-epoxyethyl-10,11-epoxyoctadecanedioate; dibutyl 3-butyl-3,4,5,6-diepoxycyclohexane-1,2-dicarboxylate; dicyclohexyl 3,4,5,6-diepoxycyclohexane-1,2-dicarboxylate; dibenzyl 1,2,4,5-diepoxycyclohexane-1,2-dicarboxylate and diethyl 5,6,10,11-diepoxyoctadecyl succinate.

Still another group comprises the epoxidized polyethylenically unsaturated hydrocarbons, such as epoxidized 2,2-bis(2-cyclohexenyl)propane, epoxidized vinyl cyclohexene and epoxidized dimer of cyclopentadiene.

The preferred polyepoxides are those represented by the general formula

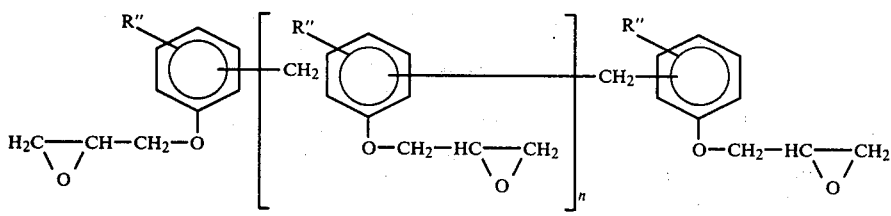

wherein each R" independently is hydrogen or an alkyl radical and n has an average value of from about 0.1 to about 10, preferably from about 1 to about 2. Prepara-

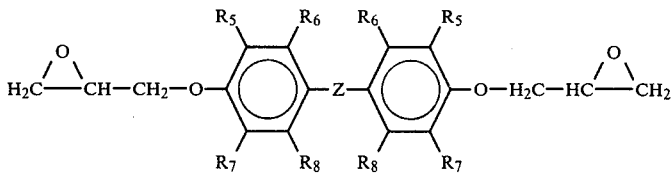

wherein $R_5$, $R_6$, $R_7$ and $R_8$ are each independently hydrogen, bromine or chlorine and wherein Z is selected from oxygen, sulfur, —SO—, —SO$_2$—, bivalent hydrocarbon radicals containing up to about 10 carbon atoms, oxygen-, sulfur- and nitrogen-containing hydrocarbon radicals, such as —OR'O—, —OR'—O—R'—O—, —S—R'—S—, and

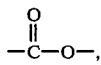

wherein R' at each occurrence is a bivalent hydrocarbon radical. "Z" preferably is an alkylene or alkylidene group having from 1 to about 4 carbon atoms. More preferably Z is isopropylidene or methylene.

Step (a):

The epoxide reactant and the isocyanatoalkyl ester containing the hydrolyzable chloride reactant are brought together with mixing in Step (a), so as to effect intimate contact in a liquid reaction medium. The order of introduction is not critical, but preferably the epoxide-containing compound is introduced into the isocyanatoalkyl ester.

The reaction may be conducted in the presence or absence of solvents or diluents. In most cases, the epoxide-containing compound and the isocyanatoalkyl ester will be liquid and the reaction can be readily effected without the addition of solvents or diluents. However, it is preferred that the reaction medium contain at least about 5 weight percent of a diluent inert to both the epoxide and isocyanate moieties present in the reaction. Examples of such inert diluents include chlorinated alkanes and benzenes, such as methylene chloride, chloroform, ethylene dichloride, chlorobenzene and the like, and inert hydrocarbons, such as, xylene, toluene, cyclohexane and the like. The preferred diluent is methylene chloride. In one preferred embodiment previously mentioned, the isocyanatoalkyl ester is utilized in the same organic solvent in which it is prepared.

Where the isocyanatoalkyl ester bears a vinyl moiety, it is advantageous to employ an effective amount of a conventional inhibitor to prevent vinyl addition polymerization. Representative inhibitors are inorganic copper salts (e.g., copper chloride), N-nitrosodiphenylamine, di-beta-naphthol, hydroquinone, p-hydroxydiphenylamine, trinitrotoluene, N,N'-diphenylphenyldiamine, 2,5-di-t-butyl hydroquinone and monomethyl ether hydroquinone. The amount of inhibitor used can vary, but typically will be from about 0.01 to about 0.2 weight percent based on the weight of the isocyanatoalkyl ester.

The epoxide-containing compound is advantageously employed in the reaction in a ratio from about 0.5 to about 2.0 equivalents of epoxide per equivalent of hydrolyzable chloride. Preferably, this ratio is in the range from about 0.75 to about 1.5 equivalents of epoxide per equivalent of hydrolyzable chloride, and more preferably about 0.9 to about 1.1 epoxy equivalents per equivalent of hydrolyzable chloride.

The temperature of the liquid reaction medium in Step (a) should desirably be in the range from about 5° C. to about 100° C., preferably about 20° C. to about 90° C., for a sufficient period to effect substantial reaction of the epoxide-containing compound with the hydrolyzable chloride. The term substantial reaction as used herein refers to the reaction of at least about 25 percent, more preferably 50 percent, of the equivalents of hydrolyzable chloride present with the epoxide-containing compound. The minimum period of contact necessary to effect substantial reaction will vary depending upon the reaction temperature, the identity of the epoxide, as well as other factors. Generally, the higher reaction temperatures within the aforementioned ranges will increase the rate of removal of the hydrolyzable chloride, but the rate of the undesirable reactions of the isocyanatoalkyl ester with the epoxide and residual water is also enhanced thereby. Typically, dependent upon the reaction parameters, a minimum contact period of from about 10 minutes to about 30 minutes is necessary to effect substantial reaction of the epoxide and hydrolyzable chloride. Of course, much longer periods of reaction can be employed as desired to effect substantially complete reaction between the epoxide and hydrolyzable chloride, so long as unacceptable reaction of the isocyanatoalkyl ester does not occur.

Isocyanatoalkyl ester is susceptible to reaction with moisture. For this reason, the reaction medium is desirably anhydrous. Moreover, the atmosphere above the reaction medium is preferably free from water and more preferably is inert in the reaction. The pressure above the medium is not critical with atmospheric pressure being convenient.

In one embodiment of this invention, following or contemporaneous with Step (a), the isocyanatoalkyl ester dissolved in a water-immiscible organic solvent is contacted with an aqueous solution of a weak base. Representative water-soluble weak bases include tertiary amines and the bicarbonate, carbonate, acetate or citrate salts of an alkali metal or ammonium. For example, sodium bicarbonate, sodium carbonate, potassium bicarbonate, potassium carbonate, lithium carbonate, lithium bicarbonate, sodium acetate, potassium acetate, sodium citrate, sodium borate, dimethylaniline, quinoline, triethylamine and tetramethylethylenediamine are suitable weak bases. The alkali metal bicarbonates are preferred and an especially preferred weak base is sodium bicarbonate. Dilute solutions, about 0.5 to about 5 percent by weight of the weak base in water are preferred. Generally, a mole ratio of from about 2 to about 10 equivalents of the weak base per equivalent of hydrolyzable chloride is employed. Generally, the contact time between the aqueous base and the isocyanatoalkyl ester should be relatively brief (typically, about 5 to 10 minutes) to minimize hydrolysis of the isocyanatoalkyl ester. Preferred temperatures are from about 0° C. to about 30° C. for this step. Higher reaction temperatures are likely to effect hydrolysis.

Step (b):

The isocyanatoalkyl ester can be conveniently recovered from the other components of the reaction mixture in Step (a) by fractional distillation of the mixture. Preferably, the distillation of the mixture to recover the isocyanatoalkyl ester immediately follows or occurs contemporaneous with the reaction of the hydrolyzable chlorides so as to minimize hydrolysis. Dependent upon the boiling point of the epoxide compound and its hydrogen chloride adduct, the epoxide and derivative are removed either in a fraction before the isocyanate ester or may be left in the undistilled residue. Typically, the preferred lower alkylene oxides and their hydrogen chloride adducts are removed in the lower boiling fractions, whereas epoxy resins will remain in the residue remaining after distillation of the isocyanatoalkyl ester. The organic diluent, if present, is also generally removed in a lower boiling fraction. The chlorohydrin of the epoxide can be recovered after distillation, dehydrochlorinated with base in a known manner and the epoxide recycled.

The distillation of the isocyanatoalkyl ester is advantageously performed at reduced pressure, preferably less than 10 millimeters of mercury, in order to effect distillation at the lowest temperature possible, thereby minimizing thermal decomposition of the isocyanatoalkyl ester. Generally, temperatures greater than 110° C. should be avoided, if possible. Of course, the distillation of the isocyanatoalkyl ester is advantageously carried out under anhydrous conditions.

Experimental:

The following examples will further illustrate the invention. All parts and percentages are by weight unless otherwise specified.

Hydrolyzable chloride determination:

Four grams of the isocyanate to be analyzed are dissolved in 25 milliliters (ml) of dry toluene. To the solution, there is added 50 ml of methanol and 5 ml of water. The mixture is refluxed for 25 minutes while stirring. Then 25 ml of methanol are added and the mixture is allowed to cool to room temperature. With stirring, there is then added 1 ml of concentrated nitric acid. The resulting mixture is then stirred for 1 minute and titrated with 0.05 N silver nitrate solution to identify the inflection point in the potentiometric titration curve. The weight percent hydrolyzable chloride is calculated according to the equation:

Percent hydrolyzable chloride = $0.0443 \times$ (ml of AgNO$_3$)

Example 1

To a reaction vessel equipped with stirring means and temperature indication means were charged 58 grams of crude 2-isocyanatoethyl methacrylate (IEM) in 262 grams of methylene chloride under a nitrogen atmosphere. This methylene chloride solution contained 0.21 percent hydrolyzable chloride. The crude IEM had been prepared by the reaction of 2-isopropenyl oxazoline with phosgene in a methylene chloride solution in the presence of an aqueous solution of sodium hydroxide. To this reaction mixture is added 0.3 gram of monomethyl ether hydroquinone (MEHQ). At a temperature of 23° C., 2.5 grams of 1,2-butylene oxide were introduced into the reaction vessel with stirring, so as to effect a 1.8:1 equivalent ratio of epoxide to hydrolyzable chloride.

The reaction vessel was then heated with a 90° C.–95° C. oil bath to distill off the methylene chloride and excess butylene oxide. A vacuum was then applied to the mixture and the IEM fraction was distilled at a temperature of 60° C. The distilled IEM contained only 0.05 percent hydrolyzable chloride, a 96 percent reduction by weight.

In contrast, crude IEM distilled in a similar manner except that no epoxide was employed contained 0.19 percent hydrolyzable chloride, a reduction of only 86 percent by weight.

EXAMPLE 2

In a manner otherwise similar to Example 1, 1.5 grams of the diglycidyl ether of 4,4'-isopropylidenediphenol (bisphenol A) were introduced in place of the butylene oxide to 54 grams of IEM and 0.3 gram of MEHQ in 266 grams of methylene chloride at 23° C. The methylene chloride solution prior to the addition of bisphenol A contained 0.083 percent hydrolyzable chloride. The equivalent ratio of epoxide to hydrolyzable chloride was 1:1. The distilled IEM after contact with the epoxide contained only 0.03 percent hydrolyzable chloride, a 98 percent reduction by weight.

In contrast, when this distillation procedure was repeated without the epoxide the same yield of IEM was obtained, but 0.11 percent hydrolyzable chloride was present by weight.

EXAMPLE 3

In a manner otherwise similar to Example 2, the crude IEM solution in methylene chloride was first partially distilled to produce a 94 gram solution containing 81 grams of IEM. The resulting solution contained 0.73 percent hydrolyzable chloride. Then 3.3 grams of the diglycidyl ether of bisphenol A were introduced into the IEM solution. The equivalent ratio of epoxide to hydrolyzable chloride was 1:1. The IEM recovered from the epoxide by distillation contained only 0.05 percent hydrolyzable chloride, a reduction of 96 percent by weight.

In contrast when the foregoing distillation procedure was repeated without the epoxide, 0.18 percent of hydrolyzable chloride was present, an 85 percent reduction by weight.

EXAMPLE 4

To a reaction vessel charged with 60 grams of substantially pure (99+ percent) IEM containing 0.16 percent of hydrolyzable chloride and 0.3 gram of MEHQ was introduced 0.50 gram of the diglycidyl ether of bisphenol A at 23° C., so as to effect a 1:1 equivalent ratio of epoxide to hydrolyzable chloride. The reaction vessel was heated in a 90° C.–95° C. oil bath for 0.5 hour under a nitrogen atmosphere and then was evacuated in order to distill the IEM. This IEM distillate contained only 0.05 percent hydrolyzable chloride.

In contrast, when the IEM was distilled without contact with the epoxide the distillate contains 0.09 percent hydrolyzable chloride.

EXAMPLE 5

In a manner otherwise similar to Example 1, 3.0 grams of sodium carbonate and 2.5 grams of butylene oxide were introduced to a solution of 43 grams of IEM and 0.3 gram of MEHQ in 277 grams of methylene chloride at 23° C. The methylene chloride solution prior to the addition of the epoxide and base contained 0.79 percent hydrolyzable chloride. The IEM recovered from this solution by fractional distillation contained only 0.34 percent hydrolyzable chloride.

In contrast, crude IEM distilled in a similar manner except that no epoxide was employed contained 1.0 percent hydrolyzable chloride. However, when crude IEM was distilled in the presence of 2.5 grams butylene oxide without sodium carbonate, the distilled IEM contained only 0.29 percent hydrolyzable chloride.

What is claimed is:

1. In a process for preparing an isocyanatoalkyl ester of an organic carboxylic acid represented by the formula

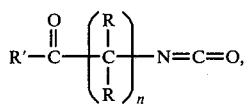

wherein each R is independently hydrogen, alkyl, alkenyl, alkoxy, alkaryl, aralkyl or aryl; R' is hydrogen, $C_1$-$C_{17}$ alkyl, $C_2$-$C_{17}$ alkenyl, $C_7$-$C_{20}$ alkaryl or $C_6$-$C_{24}$ aryl and n is 2 or 3, said process comprising the steps of reacting a 2-oxazoline or 2-oxazine with phosgene in a water-immiscible, organic solvent in the presence of an aqueous solution of a hydrogen chloride acceptor and then separating the organic solution of the resulting isocyanatoalkyl ester from the aqueous phase, the improvement comprising the steps of:

(a) contacting the isocyanatoalkyl ester in a liquid phase with a vicinal epoxide-containing compound, said epoxide-containing compound being present in a ratio of at least about 0.5 equivalent of epoxide per equivalent of hydrolyzable chloride, so as to effect substantial reaction of the epoxide-containing compound with the hydrolyzable chloride; and (b) separating the isocyanatoalkyl ester from the other components of the liquid mixture resulting from Step (a) by fractional distillation.

2. The process as described in claim 1, wherein Step (a) is conducted in the same organic solvent in which the isocyanatoalkyl ester is prepared.

3. The process as described in claim 1, which further comprises the step of separating by distillation the isocyanatoalkyl ester from the organic solution in which it is prepared and then conducting steps (a) and (b).

4. The process as described in claim 1 wherein the epoxide-containing compound is employed in step (a) in a ratio from about 0.75 to about 1.5 equivalents of epoxide per equivalent of hydrolyzable chloride.

5. The process as described in claim 3 wherein the epoxide-containing compound and the isocyanatoalkyl ester are contacted in step (a) in the presence of at least about 5 weight percent of an inert diluent.

6. The process as described in claim 5 wherein the inert diluent is methylene chloride.

7. The process as described in claim 4 wherein step (a) is conducted at a reaction temperature from about 5° C. to about 100° C.

8. The process as described in claim 1 wherein the isocyanatoalkyl ester is represented by the formula

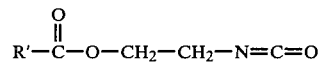

wherein R' is a $C_1$-$C_4$ alkyl or a $C_2$-$C_4$ alkenyl.

9. The process as described in claim 8 wherein R' is vinyl or isopropenyl.

10. The process as described in claim 8 wherein R' is isopropenyl.

11. The process as described in claim 7 further comprising the step of contacting the isocyanatoalkyl ester dissolved in a water-immiscible organic solvent with an aqueous solution of a weak base, following or contemporaneous with step (a).

12. The process as described in claim 7 wherein the epoxide-containing compound is ethylene oxide, 1,2-propylene oxide or 1,2-butylene oxide.

13. The process as described in claim 7 wherein the epoxide-containing compound is represented by the formula

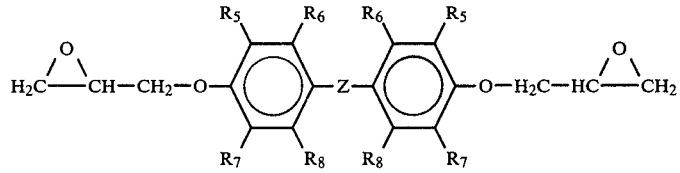

wherein $R_5$, $R_6$, $R_7$ and $R_8$ are each independently hydrogen, bromine or chlorine; Z is selected from the group consisting of oxygen, sulfur, —SO—, —SO$_2$—, bivalent hydrocarbon radicals containing up to about 10 carbon atoms, —OR'O—, —OR'—O—R'—O—, —S—R'—S— and

wherein R' is a bivalent hydrocarbon radical.

14. The process as described in claim 13 wherein Z is an alkylene or alkylidene group having from 1 to 4 carbon atoms.

15. The process as described in claim 12 or 14 wherein the isocyanatoalkyl ester is 2-isocyanatoethyl methacrylate, this reactant having been prepared by the reaction of phosgene with 2-isopropenyl-2-oxazoline in the presence of an aqueous solution of a hydrogen chloride acceptor.

* * * * *

UNITED STATES PATENT AND TRADEMARK OFFICE
CERTIFICATE OF CORRECTION

PATENT NO. : 4,310,688
DATED : January 12, 1982
INVENTOR(S) : Abel Mendoza

It is certified that error appears in the above—identified patent and that said Letters Patent is hereby corrected as shown below:

Column 2, line 27-formula, "$R'-\overset{O}{\overset{\|}{C}}\left(\overset{R}{\underset{R}{\overset{|}{\underset{|}{C}}}}\right)_n N=C=O,$" should read -- $R'-\overset{O}{\overset{\|}{C}}-O\left(\overset{R}{\underset{R}{\overset{|}{\underset{|}{C}}}}\right)_n N=C=O,$ --

Column 9, line 17-formula, "$R'-\overset{O}{\overset{\|}{C}}\left(\overset{R}{\underset{R}{\overset{|}{\underset{|}{C}}}}\right)_n N=C=O,$" should read -- $R'-\overset{O}{\overset{\|}{C}}-O\left(\overset{R}{\underset{R}{\overset{|}{\underset{|}{C}}}}\right)_n N=C=O,$ --

Signed and Sealed this

Thirteenth Day of July 1982

[SEAL]

Attest:

*Attesting Officer*

GERALD J. MOSSINGHOFF
*Commissioner of Patents and Trademarks*